US008372473B2

(12) United States Patent
Dussarrat

(10) Patent No.: US 8,372,473 B2
(45) Date of Patent: Feb. 12, 2013

(54) COBALT PRECURSORS FOR SEMICONDUCTOR APPLICATIONS

(75) Inventor: Christian Dussarrat, Wilmington, DE (US)

(73) Assignee: L'Air Liquide Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 1130 days.

(21) Appl. No.: 12/124,376

(22) Filed: May 21, 2008

(65) Prior Publication Data

US 2009/0029036 A1     Jan. 29, 2009

Related U.S. Application Data

(60) Provisional application No. 60/939,269, filed on May 21, 2007.

(51) Int. Cl.
*B05D 5/12* (2006.01)
(52) U.S. Cl. .................................. 427/96.1; 427/126.6
(58) Field of Classification Search ................ 427/96.1, 427/419.8
See application file for complete search history.

(56) References Cited

U.S. PATENT DOCUMENTS

| | | | |
|---|---|---|---|
| 3,088,361 A | 5/1963 | Lay | |
| 3,185,718 A | 5/1965 | Brown et al. | |
| 3,290,348 A | 12/1966 | Mullineaux | |
| 3,458,547 A | 7/1969 | Coffery | |
| 4,507,401 A * | 3/1985 | Dubois et al. | 502/242 |
| 4,645,849 A | 2/1987 | Lewis | |
| 4,814,294 A | 3/1989 | West et al. | |
| 4,880,670 A | 11/1989 | Erbil | |
| 5,098,516 A | 3/1992 | Norman et al. | |
| 5,130,172 A | 7/1992 | Hicks et al. | |
| 5,306,836 A | 4/1994 | Purdy | |
| 5,403,620 A | 4/1995 | Kaesz et al. | |
| 5,441,766 A | 8/1995 | Choi et al. | |
| 5,587,651 A | 12/1996 | Berkcan et al. | |
| 5,605,865 A | 2/1997 | Maniar et al. | |
| 5,767,301 A | 6/1998 | Senzaki et al. | |
| 5,851,921 A | 12/1998 | Gardner et al. | |
| 6,037,001 A | 3/2000 | Kaloyeros et al. | |
| 6,077,571 A * | 6/2000 | Kaloyeros et al. | 427/576 |
| 7,045,457 B2 | 5/2006 | Machida et al. | |
| 7,064,224 B1 | 6/2006 | Lei et al. | |
| 7,951,711 B2 | 5/2011 | Dussarrat | |
| 2003/0100162 A1 | 5/2003 | Joo | |
| 2003/0129826 A1 | 7/2003 | Werkhoven et al. | |
| 2003/0207564 A1 | 11/2003 | Ahn et al. | |
| 2004/0004247 A1 | 1/2004 | Forbes et al. | |
| 2004/0105934 A1* | 6/2004 | Chang et al. | 427/255.28 |
| 2004/0129212 A1 | 7/2004 | Gadgil et al. | |
| 2004/0241321 A1* | 12/2004 | Ganguli et al. | 427/255.28 |
| 2005/0202171 A1* | 9/2005 | Shin | 427/248.1 |
| 2006/0128150 A1 | 6/2006 | Gandikota et al. | |
| 2006/0223300 A1 | 10/2006 | Simka et al. | |
| 2006/0240187 A1 | 10/2006 | Weidman | |
| 2007/0202254 A1 | 8/2007 | Ganguli et al. | |

FOREIGN PATENT DOCUMENTS

| | | |
|---|---|---|
| EP | 0 297 348 | 1/1989 |
| JP | 9 235287 | 8/1996 |
| JP | 1996 202661 | 2/1998 |
| WO | WO 02 02574 | 1/2002 |
| WO | WO 2005 020317 | 3/2005 |
| WO | WO 2005 098938 | 10/2005 |
| WO | WO 2007 121249 | 10/2007 |
| WO | WO 2007 140813 | 12/2007 |
| WO | WO 2007 141059 | 12/2007 |

OTHER PUBLICATIONS

Kruse, et al., Chemical Communications, No. 15, pp. 921-922 (1968).
Levison et al., Journal of Chemical Society (A), pp. 96-99 (1970).
Muetterties et al., Journal of American Chemical Society, vol. 104, No. 10, pp. 2940-2942 (1982).
Gosser, Inorganic Chemistry, vol. 15, No. 6, pp. 1348-1351 (1976).
Anderson et al., Inorganic Chemistry, vol. 21, No. 5, pp. 2095-2097 (1982).
McEwen et al., Inorganic Chemistry, vol. 13, No. 12, pp. 2800-28-02 (1974).
Muetterties et al., Journal of American Chemical Society, vol. 96, No. 26, pp. 7920-7926 (1974).
Rakowski et al., Journal of American Chemical Society, vol. 99, No. 3, pp. 739-743 (1977).
Muetterties et al., Journal of American Chemical Society, vol. 98, No. 15, pp. 4665-4667 (1976).
Lane, P.A. et al.: "Metal Organic CVD of Cobalt Thin Films Using Cobalt Tricarbonyl Nitrosyl" Chem. Vap. Deposition 1998, 4, No. 5, pp. 183-188.
Maryuama, T: "Cobalt Thin Films Prepared by Chemical Vapor Deposition from Cobalt Acetylacelonates" Jpn. J. Appl. Phys., vol. 36, 1997 Pt. 2, No. 6A, pp. L705-L707.
Gross, M.E., et al.: "Organometallic chemical vapor deposition of cobalt and formation of cobalt disilicide" J. Vac. Sci. Technol. B 6 (5), Sep./Oct. 1988, pp. 1548-1552.
Dormans, G.J.M., et al.: "OMCVD of cobalt and cobalt silicide" J. Crystal Growth, vol. 114, 1991, pp. 364-372.
International Search Report for PCT/IB2008/052012.

(Continued)

*Primary Examiner* — Joseph Del Sole
*Assistant Examiner* — Kimberly A Stewart
(74) *Attorney, Agent, or Firm* — Patricia E. McQueeney

(57) ABSTRACT

Methods and compositions for depositing a cobalt containing film on one or more substrates are disclosed herein. A cobalt precursor, which comprises at least one pentadienyl ligand coupled to the cobalt for thermal stability, is introduced into a reaction chamber containing one or more substrates, and the cobalt precursor is deposited to form a cobalt containing film onto the substrate.

19 Claims, No Drawings

OTHER PUBLICATIONS

Akbayeva. "Cu(I) and Ru(II) complexes with elemental phosphorus as ligand: Synthesis and properties," Database CA [Online], Chemical Abstracts Service, Columbus, OH, retrieved from STN Database accession No. 2006:473550 & Russian J. of Coordination Chemistry, 32(5), 329-334.

Chi, et al. "Chemistry of copper (I) B-Diketonate complexes," J. of Organometallic Chemistry, 449 (1993) pp. 181-189.

Choi, et al. "Copper(I) tert-Butyl 3-Oxobutanoate complexes as precursors for chemical vapor deposition of copper," Beckman Institute for Advanced Science and Technology, U. of Illinois at Urbana, vol. 10, No. 9, pp. 2326-2328. 199.

Donnelly, et al. "Copper metallorganic chemical vapor deposition reactions of hexafluoroacetylacetonate Cu(I) vinyltrimethylsilane and bis(hexafluoroacetylacetonate) Cu(II) adsorbed on titanium nitride," J. Vac. Sci. Technol. A 11(1) Jan.-Feb. 1993, pp. 66-77.

Dubois, et al. "Selectivity and copper chemical vapor deposition," J. Electrochem. Soc., vol. 130, No. 11, Nov. 1992, pp. 3295-3299.

Macomber, et al. "($\eta^5$-cyclopentadienyl)- and ($\eta^5$-Pentamethylcyclopentadienyl)copper compounds containing phosphine, carbonyl, and $\eta^2$-acetylenic ligands," J. American Chemical Soc., vol. 105, No. 16, 1983, pp. 5325-5329.

Mansson. "Cyclopentadienylcopper reactions with organic halides in the presence of dimethyl sulfide," ACTA Chemica Scandinavica, Series B: Organic Chemistry and Biochemistry, vol. B32, No. 7, 1978, pp. 543-544.

Nielson, et al. "Development of the ReaxFF reactive force field for describing transition metal catalyzed reactions, with application to the initial stages of the catalytic formation of carbon nanotubes," J. of Physical Chemistry A, 109(3), pp. 493-499.

Written Opinion for corresponding PCT/IB2008/052012, Nov. 20, 2008.

Danish Written Opinion for Corresponding SG 200907075-6, Dec. 30, 2010.

International Search Report and Written Opinion for related PCT/IB2008/052011, Oct. 6, 2008.

* cited by examiner

COBALT PRECURSORS FOR SEMICONDUCTOR APPLICATIONS

CROSS REFERENCE TO RELATED APPLICATIONS

The present application claims the benefit of U.S. Provisional Application Ser. No. 60/939,269, filed May 21, 2007, herein incorporated by reference in its entirety for all purposes.

BACKGROUND

1. Field of the Invention

This invention relates generally to the field of semiconductor fabrication. More specifically, the invention relates to new precursors for the deposition of cobalt containing films onto substrates.

2. Background of the Invention

Cobalt silicides are compounds useful in the electronics field, particularly regarding the manufacture of integrated circuits and micro-electronics. Interest in cobalt silicides is increasing as device scale-down progresses due to their good thermal and chemical stability, low resistivity, wide process window and the small lattice mismatch to the silicon crystal lattice, which allows the cobalt silicide to be grown epitaxially on silicon.

ALD (Atomic Layer Deposition) and CVD (Chemical Vapor Deposition) are particularly useful techniques for deposition of metal and metal suicide films as compared to other methods of deposition such as physical vapor deposition (PVD) methods like sputtering, molecular beam epitaxy, and ion beam implantation. CVD may also be used to provide flexibility in the design and manufacturing of electronic devices, including the potential to reduce the number of processing phases required to provide a desired product.

ALD and CVD of various metals have been hampered by the lack of suitable precursor compounds. For example, conventional cobalt organometallic precursors, such as $Co(acac)_2$, $Co(acac)_3$ (acac: acetylacetonato ligand), $CO_2(CO)_8$, $Co(C_5H_5)_2$(cobaltocene), $Co(C_5H_5)(CO)_2$ and $Co(CO)_3(NO)$ have not demonstrated satisfactory properties for use in forming device-quality cobalt silicide films. Other precursors such as $Co(acac)_2$ and $Co(acac)_3$ have low vapor pressures and therefore require high temperatures to produce a vapor flow sufficient to support CVD or ALD. Carbonyl-containing molecules might be subject to decomposition, especially during light or heat exposure, which may lead to the evolution of the very harmful, toxic CO molecule. Phosphine-containing molecules are disqualified for the same reason. Organic phosphines are very hazardous and $PF_3$ being both toxic and might lead to undesired phosphorus contamination and fluorine-induced etching/damage. Such chemicals might therefore be subject to strict regulations. For instance, $CO_2(CO)_8$ is volatile and can produce cobalt metal coatings without the addition of a reducing agent, but is too thermally unstable to be a practical CVD precursor, giving rise to competing side reactions and decomposition during storage, even under vacuum or an inert atmosphere. Likewise, $Co(CO)_3$(NO) can be subject to unacceptable contamination with carbon and oxygen in the resulting cobalt and cobalt silicide layers when deposition is conducted at less than 350° C. or with a hydrogen flow of less than 500 standard cubic centimeters (sccm). Cobaltocene may be used to deposit cobalt films, but such films can be subject to severe carbon and oxygen contamination problems, even when hydrogen is used as a reducing agent.

Consequently there exists need for new cobalt suitable cobalt precursors for ALD and CVD applications.

BRIEF SUMMARY

Methods and precursors for depositing a cobalt containing film are described herein. In general, the disclosed precursor compounds utilize pentadienyl or cylclopentadienyl ligands to the cobalt to increase thermal stability. The methods and compositions may be used in a variety of deposition processes, and the compositions have several advantages such as thermal stability at room temperatures, and the absence of toxic phosphorus compounds. Other aspects of the methods and compositions will be described in more detail below.

In one embodiment, a method for depositing a cobalt containing film onto one or more substrate comprises introducing a cobalt precursor into a reaction chamber containing one or more substrate. The cobalt precursor has the general formula:

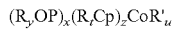

where $R_yOP$ is a pentadienyl (Op) ligand, substituted or not, with an independently selected number y of R ligands in any position on the pentadienyl ligand;

$R_tCp$ is a cylclopentadienyl (Cp) ligand, substituted or not, with an independently selected number t of R ligands in any position on the cylclopentadienyl ligand;

R is a ligand independently selected from the group consisting of an alkyl group having 1 to 4 carbon atoms, a hydrogen group, alkylamides, alkoxides, alkylsilylamides, amidinates, isonitrile, and carbonyl, and where each R may be the same or different from another R;

R' is a ligand independently selected from the group consisting of an alkyl group having 1 to 4 carbon atoms with an even number of π bonds, and where each R' may be the same or different from another R';

y is an integer ranging from 0 to 7, preferably y=2 and each R is a methyl group;

x is an integer ranging from 0 to 1;

t is an integer ranging from 0 to 5, preferably t=1, and each R is a methyl group;

z is an integer ranging from 0 to 1; and u is an integer ranging from 1 to 2.

The cobalt precursor is then deposited to form a cobalt containing film on the substrates in the reaction chamber.

In another embodiment, a first metal precursor, and at least one reaction fluid are also introduced into the reaction chamber. The reaction fluid is selected from hydrogen containing fluids, oxygen containing fluids, nitrogen containing fluids, and oxygen and nitrogen containing fluids. The cobalt precursor is reacted with the reaction fluid, and a cobalt containing film is formed on the substrate, at a temperature between about 100 and 500 C. The cobalt containing film has the general formula:

where

M is a metal or semi-metallic element;

Co is a cobalt atom, O is an oxygen atom, and N is a nitrogen atom;

$0 \leq a < 2$;

$0 \leq b \leq 2$, preferably $0.5 \leq b \leq 1.5$; and $0 \leq c \leq 1$, preferably $0 \leq c \leq 0.5$.

Other embodiments of the current invention may include, without limitation, one or more of the following features:

M in the cobalt containing film is one of magnesium (Mg), calcium (Ca), zinc (Zn), boron (B), aluminum (Al), indium (In), scandium (Sc), yttrium (Y), lanthanum (La), the rare earth metals, silicon (Si), germanium (Ge), tin (Sn), titanium (Ti), zirconium (Zr), hafnium (Hf), vanadium (V), niobium (Nb), and tantalum (Ta);

the cobalt contain film is formed on the substrate at a temperature between about 15° C. and about 35° C.

the reaction fluid is one of $O_2$, $O_3$, $H_2O$, $H_2O_2$, oxygen-containing radicals such as O. and OH., and mixtures thereof;

the reaction fluid is one of $N_2$, $NH_3$, hydrazine and its alkyl or aryl derivatives, nitrogen-containing radicals such as N., NH., $NH_2$., and mixtures thereof;

the reaction fluid is one of NO, $NO_2$, $N_2O$, $N_2O_5$, $N_2O_4$, and mixtures thereof;

the pressure in the reaction chamber is between about 1 Pa and about 100 000 Pa, preferably between about 25 Pa and about 1000 Pa;

the first metal precursor has a melting point below about 5° C., preferably below about 35 C, and more preferably the melting point is such that the metal precursor is liquid at room temperature (i.e. ~25 C);

the first metal precursor is selected from silicon containing metal precursors, germanium containing precursors, aluminum containing precursors, niobium containing precursors, and tantalum containing precursors;

the first metal precursor is selected from disiloxane, trisilylamine, disilane, and trisilane, and mixtures thereof;

the first metal precursor is selected from digermyloxane, trigermylamine, digermane, and trigermane, and mixtures thereof;

the first metal precursor is selected from trimethylaluminum, dimethylaluminum hydride, and amidoalane $AlR^1_x(NR^2R^3)_{3-x}$, wherein x ranges from 0 to 4; $R^1$, $R^2$ and $R^3$ are independently H or a C1-C6 carbon chain, either linear, branched or cyclic, and mixtures thereof;

the first metal precursor is selected from $Ta(NMe_2)_5$, $Ta(NEt_2)_4$, $Ta(NEt_2)_5$, and $Ta(=NR^1)(NR^2R^3)_3$ wherein each $R^1$, $R^2$ and $R^3$ are independently H or a C1-C6 carbon chain, either linear, branched or cyclic and where the amino ligand can have different substituents, and mixtures thereof;

the first metal precursor is selected from $Nb(NMe_2)_5$, $Nb(NEt_2)_4$, $Nb(NEt_2)_5$, $Nb(NMe_2)_4$, $Nb(NMeEt)_4$ $Nb(NMeEt)_5$, $Nb(=NR^1)(NR^2R^3)_3$ wherein each $R^1$, $R^2$ and $R^3$ are independently H or a C1-C6 carbon chain, either linear, branched or cyclic and where the amino ligand can have different substituents, and mixtures thereof.

In an embodiment, a precursor for depositing a cobalt containing film on one or more substrates has the general formula:

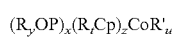

$(R_yOP)_x(R_tCp)_zCoR'_u$ where $R_yOP$ is a pentadienyl (Op) ligand, substituted or not, with an independently selected number y of R ligands in any position on the pentadienyl ligand;

$R_tCp$ is a cylclopentadienyl (Cp) ligand, substituted or not, with an independently selected number t of R ligands in any position on the cylclopentadienyl ligand;

R is a ligand independently selected from the group consisting of an alkyl group having 1 to 4 carbon atoms, a hydrogen group, alkylamides, alkoxides, alkylsilylamides, amidinates, isonitrile, and carbonyl, and where each R may be the same or different from another R;

R' is a ligand independently selected from the group consisting of an alkyl group having 1 to 4 carbon atoms with an even number of π bonds, and where each R' may be the same or different from another R';

y is an integer ranging from 0 to 7, preferably y=2 and each R is a methyl group;

x is an integer ranging from 0 to 1 t is an integer ranging from 0 to 5, preferably t=1, and each R is a methyl group;

z is an integer ranging from 0 to 1; and u is an integer ranging from 1 to 2.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct chemical bond. Thus, if a first molecule couples to a second molecule, that connection may be through a direct bond, or through an indirect bond via other functional groups or bonds. The bonds may be any known chemical bonds such as without limitation, covalent, ionic, electrostatic, dipole-dipole, etc.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation, "Me," refers to a methyl group; the abbreviation, "Et," refers to an ethyl group; the abbreviation, "Pr," refers to a propyl group; and the abbreviation, "iPr," refers to an isopropyl group.

DESCRIPTION OF PREFERRED EMBODIMENTS

In an embodiment, a cobalt precursor of the aforementioned general formula $(R_yOP)_x(R_tCp)_zCoR'_u$ is used to form a cobalt containing film of the aforementioned general formula $CoM_aO_bN_c$.

According to one embodiment, the Cp ligand may have the following formula:

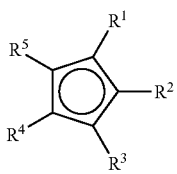

(1)

Alternatively, the Cp ligand may be represented by the formula: CpR$^{1-5}$. R$^1$-R$^5$ may each independently be a hydrogen group, a C1-C4 linear or branched alkyl group, an alkylamide group, an alkoxide group, an alkylsilylamide group, an amidinate group, a carbonyl group, or combinations thereof. R$^{1-5}$ may be the same or different from one another. Examples of suitable Cp ligands include without limitation, methylcyclopentadiene, ethylcyclopentadiene, isopropylcyclopentadiene, and combinations thereof. In at least one embodiment, at least 4 of R$^{1-}$ in the Cp ligand shown in formula (1) are hydrogen groups (i.e. unsubstituted).

In an embodiment, the Op ligand may have the following formula:

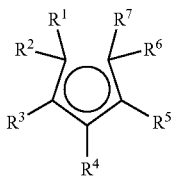

(2)

The Op ligand may alternatively be represented by the formula: OpR$^{1-7}$. R$^1$-R$^7$ may each independently be a hydrogen group, a halogen group (e.g. Cl, Br, etc.), a C1-C4 linear or branched alkyl group, an alkylamide group, an alkoxide group, an alkylsilylamide group, an amidinate group, a carbonyl group, or combinations thereof. R$^{1-7}$ may be the same or different from one another. Examples of Op ligands include without limitation, 1,3-pentadiene, 1,4-pentadiene, 3-methyl-1,3-pentadiene, 3-methyl-1,4-pentadiene, 2,4-dimethyl-1,3-pentadiene, 2,4-dimethyl-1,4-pentadiene, 3-ethyl-1,3-pentadiene, 1,5-bistrimethoxysilyl-1,3-pentadiene, and 1,5-bistrimethoxysilyl-1,4-pentadiene, and combinations thereof. In at least one embodiment, at least 5 of R$^{1-7}$ in the Op ligand shown in formula (2) are hydrogen groups (i.e. unsubstituted).

In one embodiment the cobalt precursor may be a cobalt compound having the general formula:

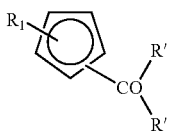

(3)

In this embodiment x equals zero. That is, the cobalt precursor comprises only the cyclopentadienyl ligand, t R ligands, and u R' ligands. There may be one R' ligand, or two as shown above in (3). The Cp may be substituted by a methyl or an ethyl. In one embodiment, the cobalt precursor is Co(RCp)(ethylene)$_2$.

In one embodiment the cobalt precursor may be a cobalt compound having the general formula:

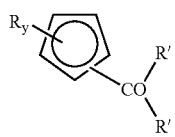

(4)

In this embodiment z equals zero. That is, the cobalt precursor comprises only the open pentadienyl ligand, y R ligands and u R' ligands. There may be only one R' ligand, or two as shown above in (4). The Op may be substituted by a methyl or an ethyl. In one embodiment, the cobalt precursor is Co(2,4,R$_2$Op)(ethylene)$_2$. In another embodiment, the precursor may be cobalt diethylene bis(2,4-dimethylpentadienyl).

Generally, the disclosed cobalt precursors have a low melting point. In at least one embodiment, the cobalt precursor is liquid at room temperature (e.g. ~25° C.). Specifically, embodiments of the precursors may have melting points less than about 50° C., alternatively less than about 40° C., alternatively less than about 35° C.

Examples of the disclosed cobalt precursors include, without limitation CoCp(ethylene)2, Co(MeCp)(ethylene)2, Co(EtCp)(ethylene)2, Co(iPrCp)(ethylene)2, CoCp(propylene)2, Co(MeCp)(propylene)2, Co(EtCp)(propylene)2, Co(iPrCp)(propylene)2, CoCp(1-butene)2, Co(MeCp)(1-butene)2, Co(EtCp)(1-butene)2, Co(iPrCp)(2-butene)2, CoCp(2-butene)2, Co(MeCp)(2-butene)2, Co(EtCp)(2-butene)2, Co(iPrCp)(2-butene)2, CoCp(butadiene)2, Co(MeCp)(butadiene)2, Co(EtCp)(butadiene)2, Co(iPrCp)(butadiene)2, CoCp(cyclobutadiene)2, Co(MeCp)(cyclobutadiene)2, Co(EtCp)(cyclobutadiene)2, Co(iPrCp)(cyclobutadiene)2, CoCp(cyclohexadi-1,3-ene)2, Co(MeCp)(cyclohexadi-1,3-diene)2, Co(EtCp)(cyclo-hexadi-1,3-diene)2, Co(iPrCp)(cyclohexadi-1,3-diene)2, CoCp(cyclohexadi-1,4-ene)2, Co(MeCp)(cyclohexadi-1,4-diene)2, Co(EtCp)(cyclohexadi-1,4-diene)2, Co(iPrCp)(cyclohexadi-1,4-diene)2, CoCp(acetylene)2, Co(MeCp)(acetylene)2, Co(EtCp)(acetylene)2, Co(iPrCp)(acetylene)2, CoCp(trimethylsilylacetylene)2, Co(MeCp)(trimethylsilylacetylene)2, Co(EtCp)(trimethylsilylacetylene)2, Co(iPrCp)(trimethylsilylacetylene)2, CoCp(bis(trimethylsilyl)acetylene)2, Co(MeCp)(trimethylsilylacetylene)2, Co(EtCp)(bis(trimethylsilyl)acetylene)2, Co(iPrCp)(bis(trimethylsilyl)acetylene)2, Co(2,4-dimethylpentadienyl)(ethylene)2, Co(2,4-dimethylpentadienyl)(propylene)2, Co(2,4-dimethylpentadienyl)(1-butylene)2, Co(2,4-dimethylpentadienyl)(2-butylene)2, Co(2,4-dimethylpentadienyl)(butadiene)2, Co(2,4-dimethylpentadienyl)(cyclobutadiene)2, Co(2,4-dimethylpentadienyl)(cyclohexa-1,3-diene)2, Co(2,4-dimethylpentadienyl)(cyclohexa-1,4-diene)2, Co(hexadienyl)(acetylene)2, Co(hexadienyl)(trimethylsilylacetylene)2, Co(hexadienyl)(bis(trimethylsilyl)acetylene)2, Co(hexadienyl)(ethylene)2, Co(hexadienyl)(propylene)2, Co(hexadienyl)(1-butylene)2, Co(hexadienyl)(2-butylene)2, Co(hexadienyl)(butadiene)2, Co(hexadienyl)(cyclobutadiene)2, Co(hexadienyl)(cyclohexa-1,3-diene)2, Co(hexadienyl)(cyclohexa-1,4-diene)2, Co(hexadienyl)(acetylene)2, Co(hexadienyl)(trimethylsilylacetylene)2, Co(hexadienyl)(bis(trimethylsilyl)acetylene)$_2$, and combinations thereof.

In some embodiments, the cobalt containing film of general formula CoM$_a$O$_b$N$_c$ is a pure cobalt metal film where a=0, b=0, and c=0, and where the cobalt precursor is one of $CoCp(CO)_2$, $Co_2(CO)_6(CH-CtBu)$, $Co(RCp)_2$ and mixtures thereof.

In some embodiments, the cobalt containing film of general formula $CoM_aO_bN_c$ is a cobalt oxide alloy film where a=0, $0 \leq b < 2$, and c=0, and where the cobalt precursor is one of $CoCp(CO)_2$, $Co_2(CO)_6(CH-CtBu)$, $Co(RCp)_2$ and mixtures thereof.

In some embodiments, the cobalt containing film of general formula $CoM_aO_bN_c$ is a cobalt nitride containing dielectric film where a=0, b=0, and $0 < c \leq 0.5$, and where the cobalt precursor is one of $CoCp(CO)_2$, $Co_2(CO)_6(CH-CtBu)$, $Co(RCp)_2$ and mixtures thereof.

In some embodiments, the cobalt containing film of general formula $CoM_aO_bN_c$ is a cobalt oxynitride containing dielectric film where a=0, $1.5 \leq b \leq 2.5$, and $0 < c \leq 0.5$, and where the cobalt precursor is one of $CoCp(CO)_2$, $Co_2(CO)_6(CH-CtBu)$, $Co(RCp)_2$ and mixtures thereof.

In some embodiments, the cobalt containing film of general formula $CoM_aO_bN_c$ is a cobalt alloy film where $0 \leq a < 1$, b=0, and c=0, and where the cobalt precursor is one of $CoCp(CO)_2$, $Co_2(CO)6(CH-CtBu)$, $Co(RCp)_2$ and mixtures thereof, M is one of Si, Ge and/or Ta.

The disclosed cobalt compounds may be deposited using any deposition methods known to those of skill in the art. Examples of suitable deposition methods include without limitation, conventional CVD, low pressure chemical vapor deposition (LPCVD), atomic layer deposition (ALD), pulsed chemical vapor deposition (P-CVD), plasma enhanced atomic layer deposition (PE-ALD), or combinations thereof. In an embodiment, a first precursor may be introduced into a reaction chamber. The reaction chamber may be any enclosure or chamber within a device in which deposition methods take place such as without limitation, a cold-wall type reactor, a hot-wall type reactor, a single-wafer reactor, a multi-wafer reactor, or other types of deposition systems under conditions suitable to cause the precursors to react and form the layers. The first precursor may be introduced into the reaction chamber by bubbling an inert gas (e.g. $N_2$, He, Ar, etc.) into the precursor and providing the inert gas plus precursor mixture to the reactor.

Generally, the reaction chamber contains one or more substrates on to which the metal layers or films will be deposited. The one or more substrates may be any suitable substrate used in semiconductor manufacturing. Examples of suitable substrates include without limitation, silicon substrates, silica substrates, silicon nitride substrates, silicon oxy nitride substrates, tungsten substrates, or combinations thereof. Additionally, substrates comprising tungsten or noble metals (e.g. platinum, palladium, rhodium or gold) may be used.

In an embodiment, a method of depositing a cobalt film on a substrate may further comprise introducing a first metal precursor into the reaction chamber. The first metal precursor may be a metal precursor containing any metal or semi-metal element, and in particular it may be one or more metals other than a Group 11 metal. For example, the first metal precursor may include without limitation, Mg, Ca, Zn, B, Al, In, Si, Ge, Sn, Ti, Zr, Hf, V, Nb, Ta, or combinations thereof. Other examples of metals include rare earth metals and lanthanides. The first metal precursor may contain silicon and/or germanium. In particular, examples of suitable first metal precursors include without limitation, trisilylamine, silane, disilane, trisilane, bis(tertiary-butylamino)silane (BTBAS), bis(diethylamino)silane (BDEAS), digermyloxane, trigermylamine, digermane, and trigermane, or combinations thereof. In addition, the first metal precursor may be an aminosilane having the formula: $SiH_x(NR^1R^2)_{4-x}$. The subscript, x, is an integer between 0 and 4. $R^1$ and $R^2$ may each independently be a hydrogen group or a C1-C6 alkyl group, either linear, branched or cyclic. $R^1$ and $R^2$ may be the same or different from on another. In one embodiment, the first metal precursor is tris(diethylamino)silane (TriDMAS).

In another embodiment, the first metal precursor may be an aluminum source. Examples of suitable aluminum sources include without limitation, trimethylaluminum, dimethylaluminum hydride, or combinations thereof. Additionally, the aluminum source may be an amidoalane having the formula: $AlR^1_x(NR^2R^3)_{3-x}$. The subscript, x, is an integer from 0 and 3. $R^1$, $R^2$, and $R^3$ may each independently be a hydrogen group or a C1-C6 carbon chain, either linear, branched or cyclic and may each be the same or different from on another.

In another embodiment, the first metal precursor may be a tantalum and/or niobium source selected from the group comprising MAC15 and corresponding adducts, $M(NMe_2)_5$, $M(NEt_2)_4$, $M(NEt_2)_5$, or combinations thereof. M represents either tantalum or niobium. Furthermore, the tantalum and/or niobium source may be an amino-containing tantalum and/or niobium source having the formula: $M(=NR^1)(NR^2R^3)_3$. $R^1$, $R^2$, and $R^3$ may each independently be a hydrogen group or a C1-C6 alkyl group, either linear, branched or cyclic.

Generally, The weight ratio of the first metal precursor to the cobalt precursor introduced into the reaction chamber may range from about 100:1 to about 1:100, alternatively from about 50:1 to about 1:50, alternatively from about 1:1 to about 10:1.

In some embodiments, the reaction chamber may be maintained at a pressure ranging from about 1 Pa to about 100,000 Pa, alternatively from about 10 Pa to about 10,000 Pa, alternatively from about 25 Pa to about 1000 Pa. In addition, the temperature within the reaction chamber may range from about 100° C. to about 500° C., alternatively from about 120° C. to about 450° C., alternatively from about 150° C. to about 350° C. Furthermore, the deposition of the metal film may take place in the presence of a reaction fluid. The reaction fluid, which may be a fluid or a gas, may be a hydrogen source, an oxygen source, a nitrogen source, or an oxygen/nitrogen source.

Examples of suitable hydrogen sources include without limitation, $H_2$, $H_2O$, $H_2O_2$, $N_2$, $NH_3$, hydrazine and its alkyl or aryl derivatives, diethylsilane, trisilylamine, silane, disilane, phenylsilane and any molecule containing Si—H bonds, dimethylaluminum hydride, hydrogen-containing radicals such as H., OH., N., NH., $NH_2$., or combinations thereof.

Examples of suitable oxygen sources include without limitation, $O_2$, $O_3$, $H_2O$, $H_2O_2$, oxygen-containing radicals such as O. and OH., and mixtures thereof.

Examples of suitable nitrogen sources include without limitation, $N_2$, $NH_3$, hydrazine and its alkyl or aryl derivatives, nitrogen-containing radicals such as NO, NH., $NH_2$., and mixtures thereof.

Examples of suitable oxygen/nitrogen sources include without limitation NO, $NO_2$, $N_2O$, $N_2O_5$, $N_2O_4$, and mixtures thereof.

In some embodiments, an inert gas may be introduced into the reaction chamber. Examples of inert gases include without limitation, He, Ar, Ne, or combinations thereof.

In some embodiments, the cobalt precursor and the first metal precursor precursors may be introduced sequentially (as in ALD) or simultaneously (as in is CVD) into the reaction chamber. In one embodiment, the first and second precursors may be pulsed sequentially or simultaneously (e.g. pulsed CVD) into the reaction chamber while the oxidizing or nitridizing gas is introduced continuously into the reaction chamber. Each pulse of the cobalt and/or first metal precursor may last for a time period ranging from about 0.01 s to about 10 S, alternatively from about 0.3 s to about 3 s, alternatively from about 0.5 s to about 2 s. In another embodiment, the reaction fluid, and/or the inert gas may also be pulsed into the reaction chamber. In such embodiments, the pulse of each gas may last for a time period ranging from about 0.01 s to about 10 s, alternatively from about 0.3 s to about 3 s, alternatively from about 0.5 s to about 2 s.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A method for depositing a cobalt containing film on to one or more substrates comprising:
   a) introducing a cobalt precursor into a reaction chamber containing one or more substrate, wherein the cobalt precursor is selected from the group consisting of: CoCp(propylene)$_2$, Co(MeCp)(propylene)$_2$, Co(EtCp)(propylene)$_2$, Co(iPrCp)(propylene)$_2$, CoCp(1-butene)$_2$, Co(MeCp)(1-butene)$_2$, Co(EtCp)(1-butene)$_2$, Co(iPrCp)(2-butene)$_2$, CoCp(2-butene)$_2$, Co(MeCp)(2-butene)$_2$, Co(EtCp)(2-butene)$_2$, Co(iPrCp)(2-butene)$_2$, CoCp(butadiene)$_2$, Co(MeCp)(butadiene)$_2$, Co(EtCp)(butadiene)$_2$, Co(iPrCp)(butadiene)$_2$, CoCp(cyclobutadiene)$_2$, Co(MeCp)(cyclobutadiene)$_2$, Co(EtCp)(cyclobutadiene)$_2$, Co(iPrCp)(cyclobutadiene)$_2$, CoCp(cyclohexadi-1,3-ene)$_2$, Co(MeCp)(cyclohexadi-1,3-diene)$_2$, Co(EtCp)(cyclo-hexadi-1,3-diene)$_2$, Co(iPrCp)(cyclohexadi-1,3-diene)$_2$, CoCp(cyclohexadi-1,4-ene)$_2$, Co(MeCp)(cyclohexadi-1,4-diene)$_2$, Co(EtCp)(cyclohexadi-1,4-diene)$_2$, Co(iPrCp)(cyclohexadi-1,4-diene)$_2$, CoCp(acetylene)$_2$, Co(MeCp)(acetylene)$_2$, Co(EtCp)(acetylene)$_2$, Co(iPrCp)(acetylene)$_2$, CoCp(trimethylsilylacetylene)$_2$, Co(MeCp)(trimethylsilylacetylene)$_2$, Co(EtCp)(trimethylsilylacetylene)$_2$, Co(iPrCp)(trimethylsilylacetylene)$_2$, CoCp(bis(trimethylsilyl)acetylene)$_2$, Co(MeCp)(trimethylsilylacetylene)$_2$, Co(EtCp)(bis(trimethylsilyl)acetylene)$_2$, Co(iPrCp)(bis(trimethylsilyl)acetylene)$_2$, Co(2,4-dimethylpentadienyl)(ethylene)$_2$, Co(2,4-dimethylpentadienyl)(propylene)$_2$, Co(2,4-dimethylpentadienyl)(1-butylene)$_2$, Co(2,4-dimethylpentadienyl)(2-butylene)$_2$, Co(2,4-dimethylpentadienyl)(butadiene)$_2$, Co(2,4-dimethylpentadienyl)(cyclobutadiene)$_2$, Co(2,4-dimethylpentadienyl)(cyclohexa-1,3-diene)$_2$, Co(2,4-dimethylpentadienyl)(cyclohexa-1,4-diene)$_2$, Co(hexadienyl)(acetylene)$_2$, Co(hexadienyl)(trimethylsilylacetylene)$_2$, Co(hexadienyl)(bis(trimethylsilyl)acetylene)$_2$, Co(hexadienyl)(ethylene)$_2$, Co(hexadienyl)(propylene)$_2$, Co(hexadienyl)(1-butylene)$_2$, Co(hexadienyl)(2-butylene)$_2$, Co(hexadienyl)(butadiene)$_2$, Co(hexadienyl)(cyclobutadiene)$_2$, Co(hexadienyl)(cyclohexa-1,3-diene)$_2$, Co(hexadienyl)(cyclohexa-1,4-diene)$_2$, Co(hexadienyl)(acetylene)$_2$, Co(hexadienyl)trimethylsilylacetylene)$_2$, Co(hexadienyl)(bis(trimethylsilyl)acetylene)$_2$, and mixtures thereof; and
   b) depositing the cobalt precursor to form a cobalt containing film on one or more substrates.

2. The method of claim 1, further comprising:
   a) introducing a first metal precursor into the reaction chamber;
   b) introducing at least one reaction fluid into the reaction chamber, wherein the reaction fluid is selected from the group consisting of hydrogen containing fluids, oxygen containing fluids, nitrogen containing fluids, and oxygen and nitrogen containing fluids;
   c) reacting the first metal precursor with the reaction fluid; and
   d) forming a cobalt containing film on the substrate, at a temperature between about 100 and 500 C, wherein the cobalt containing film has the general formula:

$$CoM_aO_bN_c$$

wherein
   M is a metal or semi-metallic element;
   Co is a cobalt atom, O is an oxygen atom, and N is a nitrogen atom;
   $0 \leq a < 2$;
   $0 \leq b \leq 2$; and
   $0 \leq c \leq 1$.

3. The method of claim 2, wherein M is a metal or semi-metallic element which comprises at least one member selected from the group consisting of: magnesium (Mg), calcium (Ca), zinc (Zn), boron (B), aluminum (Al), indium (In), scandium (Sc), yttrium (Y), lanthanum (La), the rare earth metals, silicon (Si), germanium (Ge), tin (Sn), titanium (Ti), zirconium (Zr), hafnium (Hf), vanadium (V), niobium (Nb), and tantalum (Ta).

4. The method of claim 2, wherein the cobalt containing film is formed on the substrate at a temperature between about 15° C. and about 35° C.

5. The method of claim 2, wherein the reaction fluid comprises at least one member selected from the group consisting of: $H_2$, $H_2O$, $H_2O_2$, $N_2$, $NH_3$, hydrazine and its alkyl or aryl derivatives, diethylsilane, trisilylamine, silane, disilane, phenylsilane and any molecule containing Si—H bonds, dimethylaluminum hydride, hydrogen-containing radicals such as H., N., NH., $NH_2$., and mixtures thereof.

6. The method of claim 2, wherein the reaction fluid comprises at least one member selected from the group consisting of: $O_2$, $O_3$, $H_2O$, $H_2O_2$, oxygen-containing radicals such as O. and OH., and mixtures thereof.

7. The method of claim 2, wherein the reaction fluid comprises at least one member selected from the group consisting of: of $N_2$, $NH_3$, hydrazine and its alkyl or aryl derivatives, nitrogen-containing radicals such as N., NH., $NH_2$., and mixtures thereof.

8. The method of claim 2, wherein the reaction fluid comprises at least one member selected from the group consisting of: NO, $NO_2$, $N_2O$, $N_2O_5$, $N_2O_4$, and mixtures thereof.

9. The method of claim 2, wherein the pressure in the reaction chamber is between about 1 Pa and about 100 000 Pa.

10. The method of claim 8, wherein the pressure in the reaction chamber is between about 25 Pa and about 1000 Pa.

11. The method of claim 2, wherein the first metal precursor comprises a metal precursor with a melting point below about 50 C.

12. The method of claim 11, wherein the first metal precursor comprises a metal precursor with a melting point below about 35 C.

13. The method of claim 11, wherein the first metal precursor comprises a metal precursor which is liquid at room temperature.

14. The method of claim 2, wherein the first metal precursor comprises at least one metal precursor selected form the group consisting of silicon containing metal precursors, germanium containing precursors, aluminum containing precursors, niobium containing precursors, and tantalum containing precursors.

15. The method of claim 13, wherein the first metal precursor comprises at least one member selected from the group consisting of disiloxane, trisilylamine, silane, disilane, trisilane, bis(tertiary-butylamino)silane (BTBAS), bis(diethylamino)silane (BDEAS), tris(diethylamino)silane (TriDMAS), and mixtures thereof.

16. The method of claim 13, wherein the first metal precursor comprises at least one member selected from the group consisting of digermyloxane, trigermylamine, digermane, and trigermane, and mixtures thereof.

17. The method of claim 13, wherein the first metal precursor comprises at least one member selected from the group consisting of trimethylaluminum, dimethylaluminum hydride, and amidoalane $AlR^1_x(NR^2R^3)_{3-x}$, wherein x ranges from 0 to 4; $R^1$, $R^2$ and $R^3$ are independently H or a C1-C6 carbon chain, either linear, branched or cyclic, and mixtures thereof.

18. The method of claim 13, wherein the first metal precursor comprises at least one member selected from the group consisting of $Ta(NMe_2)_5$, $Ta(NEt_2)_4$, $Ta(NEt_2)_5$, and $Ta(=NR^1)(NR^2R^3)_3$ wherein each $R^1$, $R^2$ and $R^3$ are independently H or a C1-C6 carbon chain, either linear, branched or cyclic and where the amino ligand can have different substituents, and mixtures thereof.

19. The method of claim 13, wherein the first metal precursor comprises at least one member selected from the group consisting of $Nb(NMe_2)_5$, $Nb(NEt_2)_4$, $Nb(NEt_2)_5$, $Nb(NMe_2)_4$, $Nb(NMeEt)_4$, $Nb(NMeEt)_5$, $Nb(=NR^1)(NR^2R^3)_3$ wherein each $R^1$, $R^2$ and $R^3$ are independently H or a C1-C6 carbon chain, either linear, branched or cyclic and where the amino ligand can have different substituents, and mixtures thereof.

* * * * *